United States Patent
Huang et al.

(10) Patent No.: US 10,247,813 B2
(45) Date of Patent: Apr. 2, 2019

(54) POSITIONING METHOD AND POSITIONING SYSTEM

(71) Applicant: BEIJING ZHIGU RUI TUO TECH CO., LTD., Beijing (CN)

(72) Inventors: Weicai Huang, Beijing (CN); Lin Du, Beijing (CN)

(73) Assignee: Beijing Zhigu Rui Tuo Tech Co., Ltd., Beijing (CN)

( * ) Notice: Subject to any disclaimer, the term of this patent is extended or adjusted under 35 U.S.C. 154(b) by 356 days.

(21) Appl. No.: 14/888,070

(22) PCT Filed: Jan. 22, 2014

(86) PCT No.: PCT/CN2014/071137
§ 371 (c)(1),
(2) Date: Oct. 29, 2015

(87) PCT Pub. No.: WO2015/051606
PCT Pub. Date: Apr. 16, 2015

(65) Prior Publication Data
US 2016/0084949 A1    Mar. 24, 2016

(30) Foreign Application Priority Data

Oct. 10, 2013  (CN) .......................... 2013 1 0470130

(51) Int. Cl.
*H04N 5/232*    (2006.01)
*G06K 9/00*    (2006.01)
(Continued)

(52) U.S. Cl.
CPC .............. *G01S 11/12* (2013.01); *A61B 3/113* (2013.01); *G01C 3/32* (2013.01); *G01C 21/20* (2013.01);
(Continued)

(58) Field of Classification Search
CPC ....... G01S 11/12; A61B 3/113; A61B 3/0025; A61B 3/12; G01C 3/32; G01C 21/20;
(Continued)

(56) References Cited

U.S. PATENT DOCUMENTS

| 6,396,461 | B1 * | 5/2002 | Lewis | ................ G02B 27/0093 345/7 |
| 7,742,623 | B1 * | 6/2010 | Moon | ................ G06K 9/00604 382/103 |

(Continued)

FOREIGN PATENT DOCUMENTS

| CN | 101677762 A | 3/2010 |
| CN | 101742957 A | 6/2010 |

(Continued)

OTHER PUBLICATIONS

PCT International Search Report dated Jun. 18, 2014, issued in corresponding International Application No. PCT/CN2014/071137 (8 pages).

(Continued)

*Primary Examiner* — Thai Q Tran
*Assistant Examiner* — Christopher Braniff
(74) *Attorney, Agent, or Firm* — Sheppard, Mullin, Richter & Hampton LLP

(57) ABSTRACT

Embodiments of the present application provide a positioning method and a positioning system. The method comprises: obtaining a reference direction corresponding to a user; determining that an eye of the user is gazing at an auxiliary positioning object; acquiring position information of the auxiliary positioning object; acquiring a distance of the user relative to the auxiliary positioning object; acquiring an angle of a sight line direction of the user relative to the reference direction; and obtaining position information of the user according to the position information of the (Continued)

auxiliary positioning object, the distance of the user relative to the auxiliary positioning object, the reference direction, and the angle of the sight line direction of the user relative to the reference direction.

28 Claims, 10 Drawing Sheets

(51) Int. Cl.
  *G02B 27/00* (2006.01)
  *G02B 27/01* (2006.01)
  *A61B 3/00* (2006.01)
  *G01S 11/12* (2006.01)
  *G01C 3/32* (2006.01)
  *G01C 21/20* (2006.01)
  *A61B 3/113* (2006.01)
  *G02B 7/28* (2006.01)
  *G02B 3/14* (2006.01)
  *G06T 19/00* (2011.01)
  *A61B 3/12* (2006.01)

(52) U.S. Cl.
  CPC ............... *G02B 3/14* (2013.01); *G02B 7/287* (2013.01); *G02B 27/0093* (2013.01); *G02B 27/017* (2013.01); *G02B 27/0172* (2013.01); *G06K 9/0061* (2013.01); *G06K 9/00604* (2013.01); *G06T 19/006* (2013.01); *H04N 5/23219* (2013.01); *A61B 3/0025* (2013.01); *A61B 3/12* (2013.01); *G02B 2027/014* (2013.01); *G02B 2027/0138* (2013.01); *G02B 2027/0178* (2013.01); *G02B 2027/0187* (2013.01); *G06K 2209/05* (2013.01)

(58) Field of Classification Search
  CPC ...... G02B 3/14; G02B 7/287; G02B 27/0093; G02B 27/017; G02B 27/0172; G02B 2027/0138; G02B 2027/014; G02B 2027/0178; G02B 2027/0187; G06T 19/006; H04N 5/23219; G06K 9/00604; G06K 9/0061; G06K 2209/05
  See application file for complete search history.

(56) References Cited

U.S. PATENT DOCUMENTS

| | | | |
|---|---|---|---|
| 8,259,169 | B2 | 9/2012 | Sugio et al. |
| 2008/0048931 | A1 | 2/2008 | Ben-Ari |
| 2010/0165093 | A1* | 7/2010 | Sugio ..................... A61B 3/113 348/78 |
| 2011/0310238 | A1 | 12/2011 | Koh et al. |
| 2012/0294478 | A1* | 11/2012 | Publicover ......... G06K 9/00604 382/103 |

FOREIGN PATENT DOCUMENTS

| | | |
|---|---|---|
| CN | 102034088 A | 4/2011 |
| CN | 102135429 A | 7/2011 |
| CN | 102785620 A | 11/2012 |
| JP | H 11-31239 A | 2/1999 |

OTHER PUBLICATIONS

Office Action for Chinese Application No. 201310470130.7, dated Mar. 20, 2015, (with English Translation), 9 pages.

* cited by examiner

POSITIONING METHOD AND POSITIONING SYSTEM

CROSS-REFERENCE TO RELATED APPLICATIONS

This application is a national stage application of International Application No. PCT/CN2014/071137, filed on Jan. 22, 2014, which claims priority to and the benefit of Chinese Patent Application No. 201310470130.7, filed with the State Intellectual Property Office of P.R. China on Oct. 10, 2013, and entitled "IMAGE CAPTURING-BASED POSITIONING METHOD AND IMAGE CAPTURING-BASED POSITIONING SYSTEM". The contents of both of the above-referenced applications are herein incorporated by reference in their entirety.

TECHNICAL FIELD

The present application relates to the field of positioning technologies, and in particular, to a positioning method and system.

BACKGROUND

Positioning technologies have been widely applied, for example, the Global Positioning System (GPS) technology has been very mature, and is widely applied to fields such as navigation. However, the GPS has low positioning precision; moreover, the GPS has weak signal strength in an indoor environment, and is not suitable for indoor applications. Therefore, in recent years, many positioning methods, apparatuses and systems that are suitable for indoor environments and different from the GPS are developed. For example, positioning is implemented by fading and a transmission delay characteristic of a signal such as electromagnetic waves (Bluetooth, WIFI and the like), sound and visible light during transmission over the air. Positioning may also be implemented according to different magnetic field distributions at different spatial positions. A direction and a distance from an object and a human body to a certain determined position may be deduced by tracking the movement of the object and the human with a gyroscope and an accelerator. Moreover, positioning may also be implemented according to an image shot by a camera and having some feature objects, where objects in the image have recognizable features and are located at specific positions, and therefore, the shot image may be recognized first, and positioning may be implemented by deducing the position of the camera apparatus according to the image.

Mobile terminals having camera functions are very popular recently, and are easy to implement. Therefore, the positioning method based on an image shot by a camera has many applications, for example, US patent applications No. US20120176491 A1 and US20120209513 A2 both propose positioning technologies based on an image shot by a camera.

However, the greatest problem of positioning based on an imaged shot by a camera is that: when the camera shoots an image, the position of the camera cannot be equivalent to the position of the shot image, and therefore, after the position of the shot image is determined, relative positions of the camera and the shot image need to be determined; otherwise, the positioning precision declines.

SUMMARY

An objective of the present application is to provide a positioning method and system, so as to improve precision of image capturing-based positioning.

To achieve the above objective, in a first aspect, the present application provides a positioning method, comprising:
acquiring a reference direction corresponding to a user;
determining that an eye of the user is gazing at an auxiliary positioning object;
acquiring position information of the auxiliary positioning object;
acquiring a distance of the user relative to the auxiliary positioning object;
acquiring an angle of a sight line direction of the user relative to the reference direction; and
obtaining position information of the user according to the position information of the auxiliary positioning object, the distance of the user relative to the auxiliary positioning object, the reference direction, and the angle of the sight line direction of the user relative to the reference direction.

In a second aspect, the present application further provides a positioning system, comprising:
a reference direction acquisition module, configured to acquire a reference direction corresponding to a user;
a gaze determining module, configured to determine that an eye of the user is gazing at an auxiliary positioning object;
an object information acquisition module, configured to acquire position information of the auxiliary positioning object;
a distance acquisition module, configured to acquire a distance of the user relative to the auxiliary positioning object;
an angle acquisition module, configured to acquire an angle of a sight line direction of the user relative to the reference direction; and
a positioning module, configured to obtain position information of the user according to the position information of the auxiliary positioning object, the distance of the user relative to the auxiliary positioning object, the reference direction, and the angle of the sight line direction of the user relative to the reference direction.

In at least one technical solution of the embodiments of the present application, precise positioning is performed by acquiring a distance and a relative direction between a user and an auxiliary positioning object which an eye of the user is gazing at, to obtain a position of the user, thereby improving the precision of image capturing-based positioning.

DETAILED DESCRIPTION

The method and apparatus of the technical solutions of the present application are described in detail below with reference to the accompanying drawings and embodiments.

Figure 1:
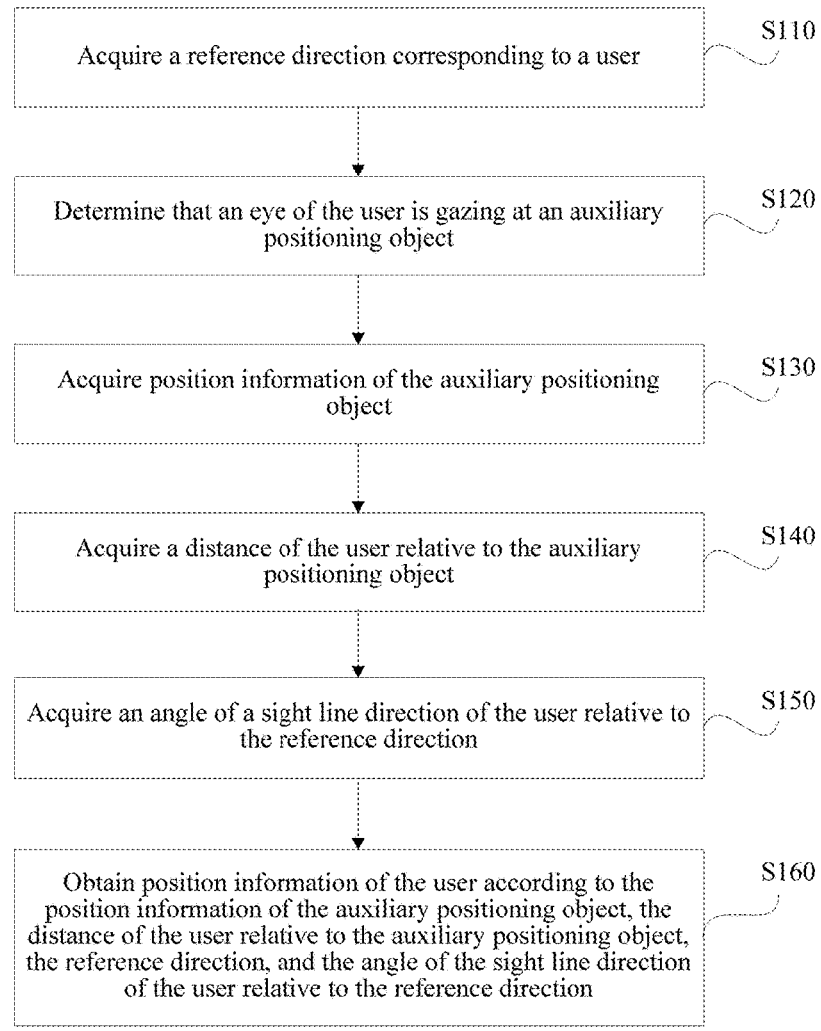
FIG. 1 is a flowchart of a positioning method according to an embodiment of the present application.

In a manner of performing positioning by using an image capturing method, some auxiliary positioning objects are selected in advance, where the auxiliary positioning objects may be ordinary objects (for example, a vase) at fixed positions, and may also be some objects having special identifiers (for example, a two-dimension code image); positions of the auxiliary positioning objects are marked and stored, and when a user takes a photo of an auxiliary positioning object of which position information is known, the auxiliary positioning object in the image is recognized, and the position information of the auxiliary positioning object is acquired for positioning the user. However, the position of the auxiliary positioning object generally is not the position where the user takes the photo, and therefore, the positioning method of directly using the position of the auxiliary positioning object as the position of the user has low precision. Therefore, it is necessary to perform precise positioning to obtain a position of a user relative to an auxiliary positioning object, thereby obtaining a precise position of the user. As shown in FIG. 1, an embodiment of the present application provides a positioning method, comprising:

S110: Acquire a reference direction corresponding to a user.

S120: Determine that an eye of the user is gazing at an auxiliary positioning object.

S130: Acquire position information of the auxiliary positioning object.

S140: Acquire a distance of the user relative to the auxiliary positioning object.

S150: Acquire an angle of a sight line direction of the user relative to the reference direction.

S160: Obtain position information of the user according to the position information of the auxiliary positioning object, the distance of the user relative to the auxiliary positioning object, the reference direction, and the angle of the sight line direction of the user relative to the reference direction.

In the following descriptions of the embodiments of the present application, the "reference direction" refers to a geographic direction, for example, east, south, west and north, and may also be a direction of another definition. The reference direction corresponding to the user is a geographic direction corresponding to a certain relative direction of the user, for example, for a geographic direction corresponding to the front direction of the user, the acquiring the reference direction corresponding to the user is: acquiring the geographic direction corresponding to the front direction of the user.

In the following descriptions of the embodiments of the present application, the "sight line direction of the user" is a direction of a sight line of the user relative to the user. For example, the sight line direction is a direction rotated by 30 degrees clockwise from the front direction of the user.

In the embodiments of the present application, precise positioning is performed by acquiring a distance and a relative direction between a user and an auxiliary positioning object which an eye of the user is gazing at, to obtain a position of the user relative to the auxiliary positioning object, thereby improving the precision of image capturing-based positioning.

In a possible implementation of the embodiments of the present application, the S110 further comprises:

acquiring the reference direction corresponding to the user by using a direction sensor.

The direction sensor may comprise, for example, a compass, which determines the reference direction by using geomagnetism or a position of a star.

In a possible implementation of the embodiments of the present application, the compass is an electronic compass, which is installed on a portable electronic device (for example, a mobile phone or a tablet computer) or a wearable device (for example, a smart watch or a pair of smart glasses) carried by the user, and used for acquiring the reference direction corresponding to the user. In one circumstance, a relative direction between the direction indicated by the compass and the user is fixed; for example, an electronic compass is installed on the smart glasses, and the geographic direction obtained by the electronic compass is the geographic direction of the front of the smart glasses, and when the user uses the smart glasses, the geographic direction acquired by the electronic compass is the geographic direction corresponding to the front direction of the eye of the user.

In a possible implementation of the embodiments of the present application, in the S120, various methods may be used to determine whether the user is gazing at the auxiliary positioning object, for example, determining whether the eye is in a gaze state according to changes of the eye and geometric parameters at the center of an eyeball, or determining whether the eye is in a gaze state based on features of an image formed at the fundus (the two determining manners belong to the prior art). Then, it is determined, according to a sight line direction of the user, whether the user is gazing at the auxiliary positioning object. For example, it may be determined whether the user is gazing at the auxiliary positioning object by using a method described in the article "Study on SVM-Based Detection for Gaze of a Human Eye" published in the Journal of Optoelectronics Laser, Vol. 15 No. 10, in October, 2004.

In order to help the user to notice the auxiliary positioning object and gaze at it, in a possible implementation of the embodiments of the present application, the method further comprises:

guiding the user to gaze at the auxiliary positioning object.

For example, in a possible implementation, the auxiliary positioning object may be marked to guide the user to gaze at the auxiliary positioning object. For example, by using text or a special symbol on an object, the user is reminded that the object is an auxiliary positioning object; for another example, by setting a signal sending apparatus on an auxiliary positioning object, a signal sent by the signal sending apparatus can be received near the auxiliary positioning object, thereby guiding the user to gaze at the auxiliary positioning object.

In addition, in a possible implementation, the auxiliary positioning object may be marked by means of augmented reality, to guide the user to gaze at the auxiliary positioning object. For example, a pair of smart glasses may be used to provide some prompts related to the auxiliary positioning object (for example, a two-dimensional code adhered at a fixed position, or an object placed at a fixed position) in the field of view by means of augmented reality, to guide a focal point of a human eye to fall on the auxiliary positioning object.

In a possible implementation, in the S130, the position information of the auxiliary positioning object is obtained by using the at least one image. Therefore, in this implementation, the S130 comprises:

capturing at least one image comprising the auxiliary positioning object.

In a possible implementation of the embodiments of the present application, when capturing the at least one image comprising the auxiliary positioning object, the image may be captured in a direction directly facing the auxiliary positioning object, or the capturing may be performed at a certain inclination angle.

To make sure that the image captured by the user comprises the auxiliary positioning object, and to facilitate recognition of the auxiliary positioning object in the image, in a possible implementation of the embodiments of the present application, the image capturing direction may be adjusted according to the sight line direction of the user. For example, by adjusting a shooting gesture of the image capturing apparatus, the image capturing direction is adjusted to be consistent with the sight line direction of the user; in this way, the image is captured with an object gazed at by the eye of the user as a center, so that subsequent recognition of the auxiliary positioning object in the image is more convenient.

In a possible implementation, the reference direction may also be set to be consistent with the image capturing direction. If the image capturing direction is also consistent with the sight line direction of the user, the geographic direction of the sight line direction of the user is the reference direction.

In the embodiment of the present application, in the S130, there are various methods for acquiring the position information of the auxiliary positioning object according to the at least one image. For example:

In a possible implementation, the S130 comprises:
sending the at least one image to an external device; and
receiving, from the external device, the position information of the auxiliary positioning object.

For example, the position information of the auxiliary positioning object is acquired by using an external positioning server. At least one image comprising the auxiliary positioning object and position information of the auxiliary positioning object corresponding to the stored image may be stored in the positioning server.

Specifically, in the method of the embodiments of the present application, the at least one image is sent to the external positioning server, and after the positioning server receives the at least one image, the positioning server searches for a pre-stored image having a highest matching degree in an image library (the image library comprises, for example, a pre-stored image comprising the auxiliary positioning object and pre-stored images corresponding to other auxiliary positioning objects); position information corresponding to the auxiliary positioning object in the at least one image may be acquired according to the pre-stored image having the highest matching degree, and the positioning server returns the position information to the user side, for example, sends the position information to a portable or wearable intelligent device carried by the user.

In addition to the above method, the positioning server may further acquire the position information corresponding to the auxiliary positioning object in the at least one image by using other suitable methods.

In addition to acquiring the position information of the auxiliary positioning object by using the external positioning server, the position information of the auxiliary positioning object may also be acquired by locally storing at least one pre-stored image comprising the auxiliary positioning object and position information of the auxiliary positioning object corresponding to the at least one pre-stored image, and analyzing the at least one image. Specifically, in a possible implementation, the S130 comprises:

pre-storing at least one pre-stored image shot in at least one determined direction and comprising the auxiliary positioning object.

The image analysis performed locally is basically similar to the image analysis performed at the side of the positioning server, and is not described in detail herein.

In a possible implementation, the S130 comprises:
recognizing the auxiliary positioning object in the at least one image; and
acquiring pre-stored position information of the auxiliary positioning object.

In one embodiment of the present application, in addition to obtaining the position information by searching the image library for the pre-stored image matching the at least one image, it is also feasible to pre-store position information corresponding to the auxiliary positioning object, recognize the auxiliary positioning object in the at least one image, and then find the position information of the corresponding auxiliary positioning object in the pre-stored information.

In a possible implementation of the embodiments of the present application, in the S140, there are various methods for acquiring the distance of the user relative to the auxiliary positioning object, for example, the distance is acquired by means of an ultrasonic range finder, a laser range finder, or the like. In one embodiment of the present application, the S140 comprises: when it is determined that the eye of the user is gazing at the auxiliary positioning object, photographing the eye of the user to acquire the distance of the user relative to the auxiliary positioning object. By photographing the eye, the sight line direction of the eye may also be acquired. Therefore, in the embodiments of the present application, photographing the eye of the user to acquire the distance of the user relative to the auxiliary positioning object is used to illustrate the embodiment of the present application.

In the embodiments of the present application, there are various manners for shooting and analyzing the eye image to obtain the distance, comprising, for example, one of the following methods:

i) A pupil direction detector is used to detect an optical axis direction of an eye, then a depth sensor (for example, infrared distance measurement) is used to obtain depth information of each object in the field of view of the eye, and an object at which the user is gazing in the field of view may be determined. This technology belongs to the prior art, and is not repeated herein in this implementation. In the embodiments of the present application, the distance of the user relative to the auxiliary positioning object may be obtained according to the depth information of the object in the field of view.

ii) Optical axis directions of two eyes are separately detected, then sight line directions of the two eyes of the user are obtained according to the optical axis directions of the two eyes, and a position of a gaze point of sight lines of the eyes relative to the user is obtained according to an intersection of the sight line directions of the two eyes. This technology also belongs to the prior art, and is not described in detail herein. In the embodiments of the present application, according to the position of the gaze point of sight lines of the eyes relative to the user, the distance of the user relative to the auxiliary positioning object can be obtained by means of geometric calculation.

iii) According to optical parameters of an optical path between a fundus image capturing unit and an eye and optical parameters of the eye when a fundus image captured corresponding to an image presented on an imaging surface of the eye satisfying at least one set resolution criterion, a distance of a gaze point of a sight line of the eye relative to the user is obtained. In one embodiment of the present application, detailed procedures of the method are described in the following, and are not described in detail herein.

Persons skilled in the art may know that, in addition to the methods in the foregoing forms, other methods for detecting a distance of a gaze point of an eye of a user relative to the user may also be applied to the method in the embodiments of the present application.

Detecting a current gaze point position of the user by using the method iii) comprises:

S141: Capture at least one fundus image of the eye.

S142: Adjust imaging parameters of an optical path between a fundus image capturing position of the at least one fundus image and the eye, until a fundus image satisfying at least one set resolution criterion is captured.

S143: Analyze the at least one image to obtain imaging parameters of the optical path and optical parameters of the eye corresponding to the fundus image, and acquiring a distance of a current gaze point of the user relative to the user according to the imaging parameters and the optical parameters of the eye.

The resolution criterion described herein may be set according to resolution measurement parameters commonly used by persons skilled in the art, for example, parameters such as effective resolution of an image, which is not described in detail herein.

In this embodiment, the at least one fundus image of the eye is analyzed and processed, to obtain the optical parameters of the eye when the fundus image satisfying at least one set resolution criterion is captured, and the imaging parameters of the corresponding optical path are acquired as well, thereby obtaining the distance of the current focus point of the sight line relative to the user by means of calculation.

The image presented at the "fundus" is mainly an image presented on the retina, which may be an image of the fundus, or may be an image of another object projected to the fundus, for example, a light spot pattern mentioned in the following.

In the S142, by adjusting the focal length of at least one optical device on the optical path and/or the position of the at least one optical device on the optical path, the fundus image satisfying at least one set resolution criterion may be acquired when the optical device is at a certain position or in a certain state. The adjustment may be continuous real-time adjustment.

In a possible implementation of the method in the embodiments of the present application, the optical device may be a focal-length adjustable lens, configured to adjust the focal length thereof by adjusting the refractive index and/or shape of the optical device. Specifically: 1) the focal length is adjusted by adjusting the curvature of at least one side of the focal-length adjustable lens, for example, the curvature of the focal-length adjustable lens is adjusted by adding or reducing liquid medium in a cavity formed by two transparent layers; and 2) the focal length is adjusted by changing the refractive index of the focal-length adjustable lens, for example, a specific liquid crystal medium is filled in the focal-length adjustable lens, and arrangement of the liquid crystal medium is adjusted by adjusting a voltage of a corresponding electrode of the liquid crystal medium, thereby changing the refractive index of the focal-length adjustable lens.

In another possible implementation of the method in the embodiments of the present application, the optical device may be: a lens assembly, configured to adjust relative positions between lenses in the lens assembly so as to adjust the focal length of the lens assembly. Alternatively, one or more lenses in the lens assembly are the focal-length adjustable lenses described above.

In addition to changing the imaging parameters of the system by changing characteristics of the optical device as described above, the imaging parameters of the system may also be changed by adjusting the position of the optical device on the optical path.

In addition, in a method of the embodiments of the present application, the S143 further comprises:

S1431: Analyze the at least one fundus image, to find the fundus image satisfying at least one set resolution criterion.

S1432: Calculate optical parameters of the eye according to the fundus image satisfying at least one set resolution criterion, and imaging parameters of the optical path already known when the fundus image satisfying at least one set resolution criterion is obtained.

The adjustment in the S142 ensures that a fundus image satisfying at least one set resolution criterion can be captured, but the S143 is needed to find the fundus image satisfying at least one set resolution criterion in the at least one fundus image, and the optical parameters of the eye may be calculated according to the fundus image satisfying at least one set resolution criterion and the known imaging parameters of the optical path.

Figure 2A:
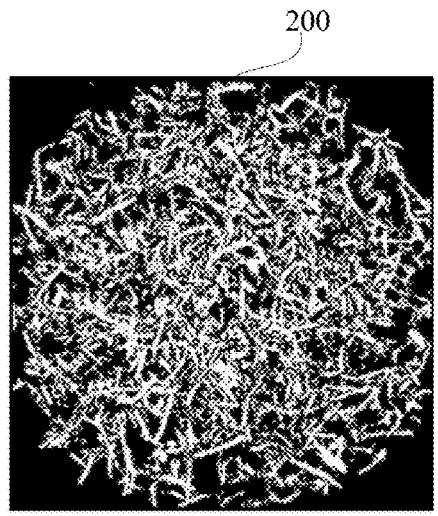
FIG. 2a is a schematic diagram of a light spot pattern used in a positioning method according to an embodiment of the present application.
Figure 2B:
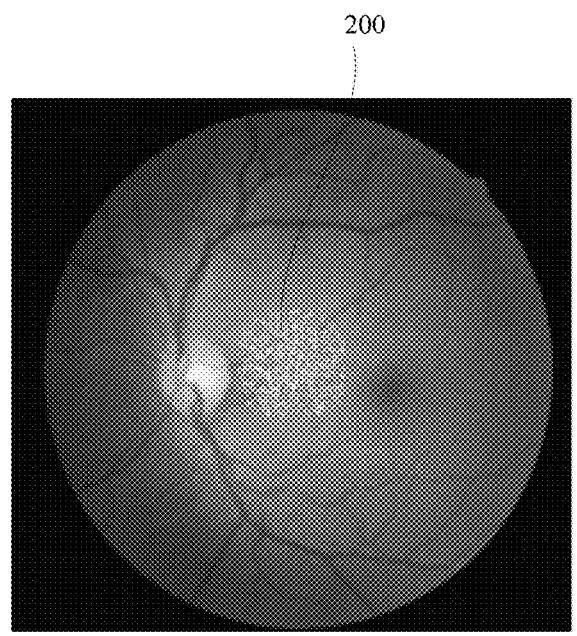
FIG. 2b is a schematic diagram of a fundus image having a light spot pattern and shot by using a positioning method according to an embodiment of the present application.

In the method of the embodiment of the present application, the S143 may further comprise:

S1433: Project a light spot to the fundus. The projected light spot may have no specific patterns but is only used for lightening the fundus. The projected light spot may also be a light spot pattern with abundant features. The pattern with abundant features may be conducive to detection, and improve the detection precision. FIG. 2a is an exemplary diagram of a light spot pattern 200, where the pattern may be formed by a light spot pattern generator, for example, frosted glass; and FIG. 2b shows a fundus image captured when the light spot pattern 200 is projected.

To avoid affecting normal viewing of the eye, the light spot is an infrared light spot invisible to the eye. Moreover, in order to reduce interference of other spectrums, a step of filtering out light, except for light that can transmit through an eye-invisible light transmission filter, in the projected light spot may be performed.

Correspondingly, one method of the embodiment of the present application may further comprise the following:

S1434: Control the brightness of the projected light spot according to a result of the analysis of the S1431. The result of the analysis comprises, for example, characteristics of the image captured in the S141, including the contrast of image features, texture features, and the like.

It should be noted that, a special situation of controlling the brightness of the projected light spot is starting or stopping the projection, for example, when the user gazes at a point continuously, the projection may be stopped periodically; when the fundus of the user is bright enough, the projection may be stopped, and the distance from the current focus point of the sight line of the eye to the eye is detected by using fundus information.

In addition, the brightness of the projected light spot may be controlled according to ambient light.

In the method of the embodiment of the present application, the S143 further comprises:

S1435: Calibrate the fundus image to obtain at least one reference image corresponding to the image presented at the fundus. Specifically, comparison calculation is performed on the at least one image and the reference image, so as to obtain the fundus image satisfying at least one set resolution criterion. Here, the fundus image satisfying at least one set resolution criterion may be an obtained image having a minimum difference with the reference image. In one method of this implementation, a difference between the currently acquired image and the reference image is calculated by using an existing image processing algorithm, for example, using a classical phase difference automatic focusing algorithm.

In one embodiment of the present application, the optical parameters of the eye obtained in the S1432 may comprise an optical axis direction of the eye (in the following descriptions of the embodiment of the present application, the optical axis direction of the eye is a direction of the optical axis of the eye relative to a certain reference plane of the user, for example, a direction relative to the front of the user) obtained according to the features of the eye when the fundus image satisfying at least one set resolution criterion is captured. The sight line direction of the user may be obtained according to the optical axis direction. Here, the features of the eye may be acquired from the fundus image satisfying at least one set resolution criterion, or may be acquired in other manners. Specifically, the optical axis direction of the eye is obtained according to features of the fundus when the fundus image satisfying at least one set resolution criterion is obtained. Determining the optical axis direction of the eye according to the features of the fundus is more precise.

When a light spot pattern is projected to the fundus, the area of the light spot pattern may be greater than that of a visible region of the fundus or smaller than that of the visible region of the fundus, where:

when the area of the light spot pattern is smaller than or equal to that of the visible region of the fundus, a classical feature point matching algorithm (for example, Scale Invariant Feature Transform (SIFT) algorithm) may be used to determine the optical axis direction of the eye by detecting a position of the light spot pattern on the image relative to the fundus.

When the area of the light spot pattern is larger than that of the visible region of the fundus, the optical axis direction of the eye may be determined according to a position of the light spot pattern on the image relative to an original light spot pattern (acquired by means of image calibration), so as to determine a sight line direction of an observer.

In another possible implementation of a method in the embodiment of the present application, the optical axis direction of the eye may also be obtained according to features of the pupil when the fundus image satisfying at least one set resolution criterion is obtained. Here, the features of the pupil may be acquired from the fundus image satisfying at least one set resolution criterion, and may also be acquired in other manners. Obtaining the optical axis direction of the eye according to the features of the pupil belongs to the prior art, and is not described in detail herein.

Moreover, the method in the embodiments of the present application may further comprise a step of calibrating the optical axis direction of the eye, so as to determine the optical axis direction of the eye more precisely.

In the method of the embodiments of the present application, the imaging parameters of the optical path between the eye and the fundus image capturing position may comprise at least one fixed imaging parameter and at least one real-time imaging parameter, where the at least one real-time imaging parameter is parameter information about the optical device when the fundus image satisfying at least one set resolution criterion is acquired, and the parameter information may be obtained by means of real-time recording when the fundus image satisfying at least one set resolution criterion is acquired.

After the current optical parameters of the eye are obtained, the distance from the eye focus point to the eye of the user may be calculated (specific procedures will be described in detail with reference to the apparatus part).

In a possible implementation of the embodiments of the present application, if the sight line direction of the user (for example, the distance acquired by means of ultrasonic waves) is not acquired in the S140, the method of the embodiment of the present application further comprises a step of acquiring the sight line direction of the user. In the prior art, there are many methods for acquiring a sight line direction of a user, which are not described in detail herein.

After the sight line direction of the user and the reference direction are acquired, in the S150 of one embodiment of the present application, an angle of the sight line direction of the user relative to the reference direction can be calculated.

For example, the sight line direction of the user is a direction rotated by 30 degrees clockwise from the front direction of the user; the reference direction is a direction rotated by 90 degrees clockwise from the front direction of the user, and the angle of the sight line direction of the user relative to the reference direction is 60 degrees anticlockwise.

Figure 3:
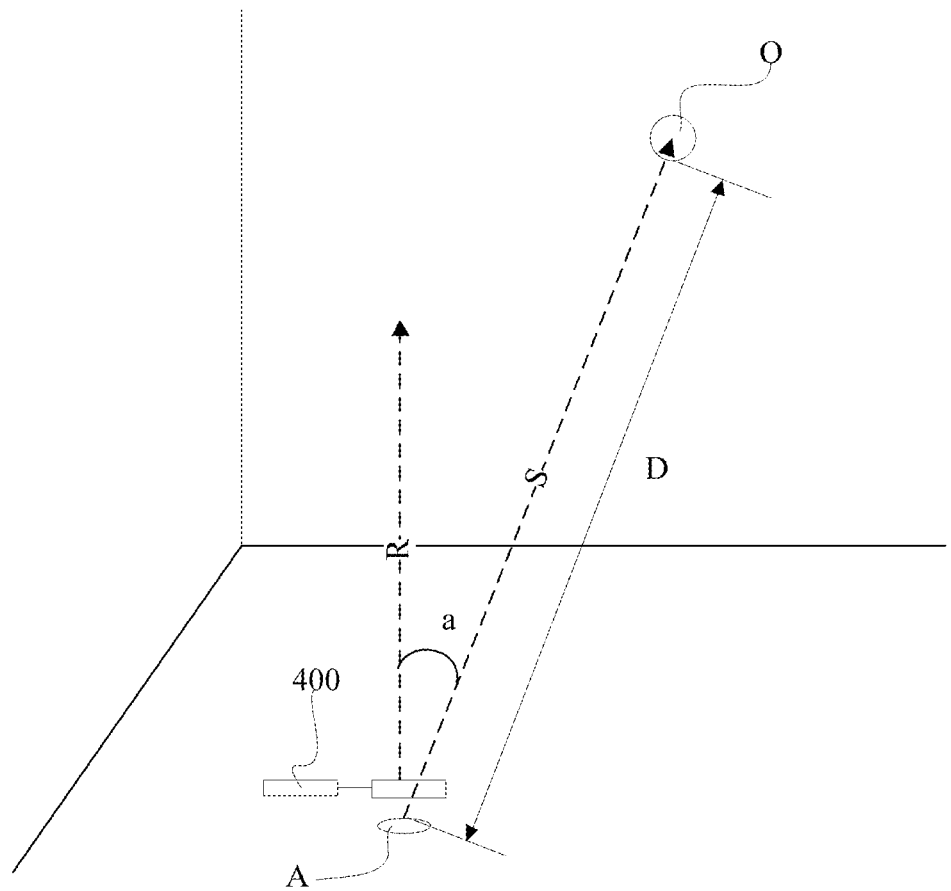
FIG. 3 is schematic diagram of an application of a positioning method according to an embodiment of the present application.

As shown in FIG. 3, in the embodiments of the present application, in the S160, a geographic direction of the sight line direction of the user may be obtained according to the reference direction R as well as an angle a of the sight line direction S of the user relative to the reference direction R; because the sight line direction S of the user points to the auxiliary positioning object O, direction information of the user relative to the auxiliary positioning object O can be obtained according to the geographic direction of the sight line direction S of the user. Further, according to the position information of the auxiliary positioning object O and the distance D of the user relative to the auxiliary positioning object, position information of the user can be calculated.

In some possible implementations of the embodiments of the present application, considering that the precision of a positioning result is affected when an included angle is formed between the sight line direction of the eye and a horizontal plane, in the method of the present application, the positioning result may further be modified by a certain extent after the included angle is determined by using, for example, a three-dimensional direction sensor or an image processing method, so that the positioning result is more precise.

It should be understood that, in various embodiments of the present application, the serial numbers of the steps do not represent the sequence of performing the steps, and the sequence of performing the processes should be determined by functions and internal logic thereof, and should not constitute any limit to the implementation process of the embodiment of the present application.

Figure 4:
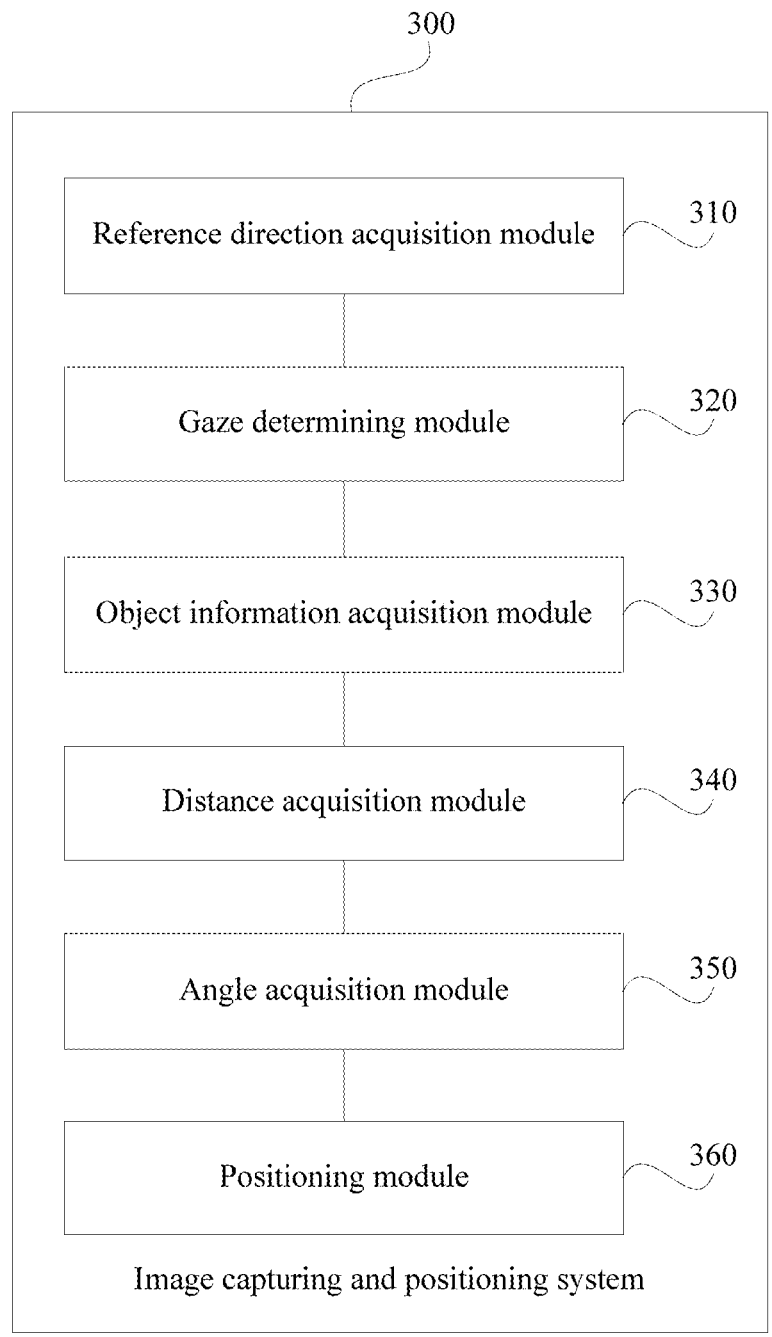
FIG. 4 is a schematic structural block diagram of a positioning system according to an embodiment of the present application.

As shown in FIG. 4, the present application further provides a positioning system 300, comprising:

a reference direction acquisition module 310, configured to acquire a reference direction corresponding to a user;

a gaze determining module 320, configured to determine that an eye of the user is gazing at an auxiliary positioning object;

an object information acquisition module 330, configured to acquire position information of the auxiliary positioning object;

a distance acquisition module 340, configured to acquire a distance of the user relative to the auxiliary positioning object;

an angle acquisition module 350, configured to acquire an angle of a sight line direction of the user relative to the reference direction; and a positioning module 360, configured to obtain position information of the user according to the position information of the auxiliary positioning object, the distance of the user relative to the auxiliary positioning object, the reference direction, and the angle of the sight line direction of the user relative to the reference direction.

In the embodiments of the present application, precise positioning is performed by acquiring a distance and a relative direction between a user and an auxiliary positioning object which an eye of the user is gazing at, to obtain a position of the user relative to the auxiliary positioning object, thereby improving the precision of image capturing-based positioning.

Figure 4A:
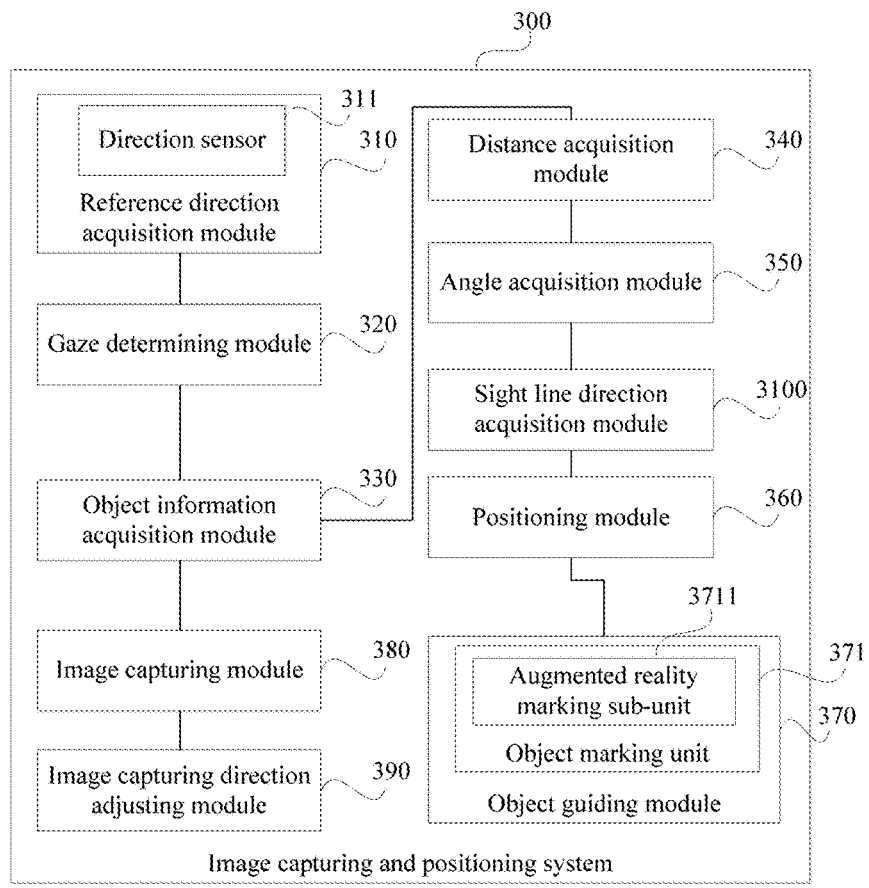
FIG. 4a is a schematic structural block diagram of another positioning system according to an embodiment of the present application.
Figure 4B:
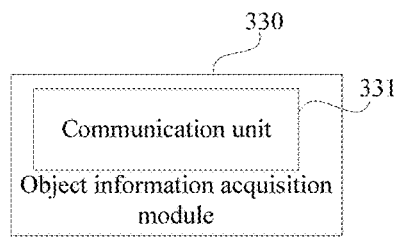
FIG. 4b and FIG. 4c are schematic structural block diagrams of two object information acquisition modules according to an embodiment of the present application.

As shown in FIG. 4a, in a possible implementation of the embodiments of the present application, the reference direction acquisition module 310 further comprises:

a direction sensor 311, configured to acquire the reference direction corresponding to the user.

The direction sensor may comprise, for example, a compass, which determines the reference direction by using geomagnetism or a position of a star.

In a possible implementation of the embodiments of the present application, the compass is an electronic compass, which is disposed in a portable electronic device (for example, a mobile phone or a tablet computer) or a wearable device (for example, a smart watch or a pair of smart glasses) carried by the user, and used for acquiring the reference direction corresponding to the user. In one circumstance, a relative direction between the direction indicated by the compass and the user is fixed, for example, an electronic compass is disposed on the smart glasses, and the geographic direction obtained by the electronic compass is the geographic direction of the front of the smart glasses, and when the user uses the smart glasses, the geographic direction acquired by the electronic compass is the geographic direction corresponding to the front direction of the eye of the user.

In the embodiments of the present application, the gaze determining module 320 may be any one of various structures for determining whether the user is gazing at the auxiliary positioning object, for example, a structure for determining, according to changes of the eye and geometric parameters at the center of the eyeball, whether the user is gazing at an object, or a structure for determining, based on features of the image formed at the fundus, whether the user is gazing at an object (the two structures belong to the prior art). Then, it is determined, according to a sight line direction of the user, whether the object gazed at by the user is the auxiliary positioning object.

In order to help the user to notice the auxiliary positioning object and gaze at it, in a possible implementation of the embodiments of the present application, the system 300 further comprises:

an object guiding module 370, configured to guide the user to gaze at the auxiliary positioning object.

In this embodiment, the function of the object guiding module is implemented according to the corresponding description in the method embodiment shown in FIG. 1, and is not repeated in this embodiment.

In a possible implementation, the object guiding module 370 further comprises:

an object marking unit 371, configured to mark the auxiliary positioning object.

In a possible implementation of the embodiments of the present application, the system 300 may be a portable or wearable device having a mixed reality function, for example, a pair of smart glasses. In a possible implementation of the embodiments of the present application, the object marking unit 371 comprises:

an augmented reality marking sub-unit 3711, configured to mark the auxiliary positioning object by means of augmented reality.

For example, on an image comprising the auxiliary positioning object and shot in real time by a pair of smart glasses, the auxiliary positioning object is marked by means of augmented reality such as highlighting, or displaying a symbol or text. The function of the unit is implemented according to the corresponding description in the method embodiment shown in FIG. 1, and is not described in detail herein.

In a possible implementation of the embodiments of the present application, the object information acquisition module 330 obtains the position information of the auxiliary positioning object by using the at least one image. Therefore, in this implementation, the system 300 further comprises:

an image capturing module 380, configured to capture at least one image comprising the auxiliary positioning object.

The object information acquisition module 330 obtains the position information of the auxiliary positioning object according to the at least one image.

In a possible implementation of the embodiments of the present application, the image capturing module 380 may be a camera on a pair of smart glasses, or may also be a camera module on a portable device carried by the user.

To make sure that the image captured by the image capturing module 380 comprises the auxiliary positioning object, or to facilitate recognition of the auxiliary positioning object in the image, in a possible implementation of the embodiment of the present application, the positioning system 300 may further comprise an image capturing direction adjusting module 390, configured to adjust the image capturing direction according to the sight line direction of the user. For example, in some implementations, the image capturing direction is adjusted to be consistent with the sight line direction of the user; in this way, the image is captured with an object gazed at by the eye of the user as a center, so that subsequent recognition of the auxiliary positioning object in the image is more convenient.

As shown in FIG. 4a, in a possible implementation of the embodiments of the present application, the object information acquisition module 330 comprises a communication unit 331, configured to:

send the captured at least one image to an external device; and receive, from the external device, the direction information of the user relative to the auxiliary positioning object and/or the position information of the auxiliary positioning object.

For the method of analyzing the at least one image and acquiring the position information of the auxiliary positioning object by the external server like an external positioning server, reference may be made to the corresponding descriptions in the method embodiment shown in FIG. 1, which is not described in detail herein.

Figure 4C:
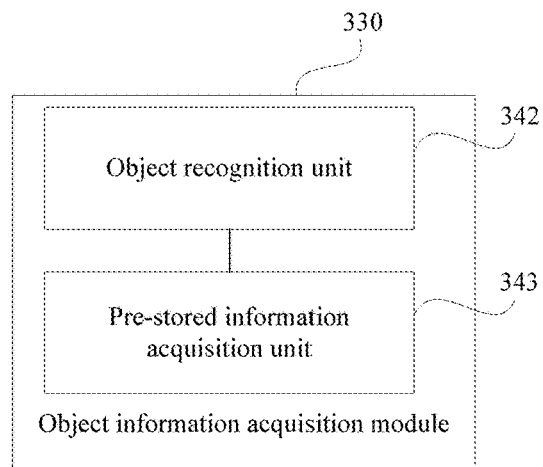

As shown in FIG. 4c, in another possible implementation of the embodiments of the present application, the object information acquisition module 330 comprises:

an object recognition unit 332, configured to recognize the auxiliary positioning object in the at least one image; and a pre-stored information acquisition unit 333, configured to acquire pre-stored position information of the auxiliary positioning object.

The functions of the units of object information acquisition module 330 are implemented according to the corresponding descriptions in the foregoing method embodiment, and are not described in detail herein.

In a possible implementation of the embodiments of the present application, the distance acquisition module 340 has various forms, including an ultrasonic range finder, a laser range finder, or the like. Moreover, in the embodiments of the present application, the distance acquisition module 340 may be an eye photographing sub-module, configured to: when it is determined that the eye of the user is gazing at the auxiliary positioning object, photograph the eye of the user to acquire the distance of the user relative to the auxiliary positioning object.

In the embodiments of the present application, the manner in which the eye photographing sub-module photographs the eye of the user and acquires the distance of the user relative to the auxiliary positioning object may be any one or more of the methods i) to iii) mentioned in the method embodiment shown in FIG. 1. The apparatus in the embodiments of the present application adopts the manner iii) having higher detection precision, and correspondingly, the eye photographing sub-module may be any one of eye photographing sub-modules shown in FIG. 5a to FIG. 5d, FIG. 6, and FIG. 7.

Persons skilled in the art may know that, in addition to the above forms of eye photographing sub-modules, other apparatuses that can be used for photographing the eye of the user and acquiring the distance of the user relative to the auxiliary positioning object may also be applied to the apparatus in the embodiments of the present application.

Figure 5A:
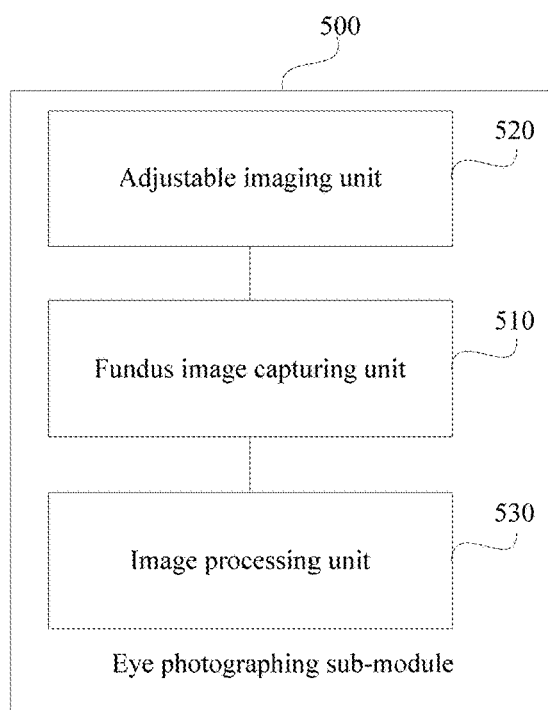
FIG. 5a is a schematic structural block diagram of an eye photographing sub-module according to an embodiment of the present application.

The eye photographing sub-module of the form iii) is further described as follows:

As shown in FIG. 5a, in a possible implementation of the embodiments of the present application, the eye photographing sub-module 500 comprises:

a fundus image capturing unit 510, configured to capture at least one fundus image of the eye;

an adjustable imaging unit 520, configured to adjust imaging parameters of an optical path between the fundus image capturing unit 510 and the eye, so that the fundus image capturing unit 521 can capture a fundus image satisfying at least one set resolution criterion; and an image processing unit 530, configured to analyze the at least one fundus image, to obtain imaging parameters of the optical path and optical parameters of the eye corresponding to the fundus image, and calculate a distance of an eye gaze point relative to the user according to the imaging parameters and the optical parameters of the eye.

In this implementation, the eye photographing sub-module 500 analyzes the at least one fundus image of the eye to obtain the optical parameters of the eye when the fundus image capturing unit captures the fundus image satisfying at least one set resolution criterion, and therefore, may calculate the distance of the current eye gaze point relative to the user.

The image presented at the "fundus" is mainly an image presented on the retina, which may be an image of the fundus, or may be an image of another object projected to the fundus. Here, the eye may be a human eye, and may also be an eye of another animal.

Figure 5B:
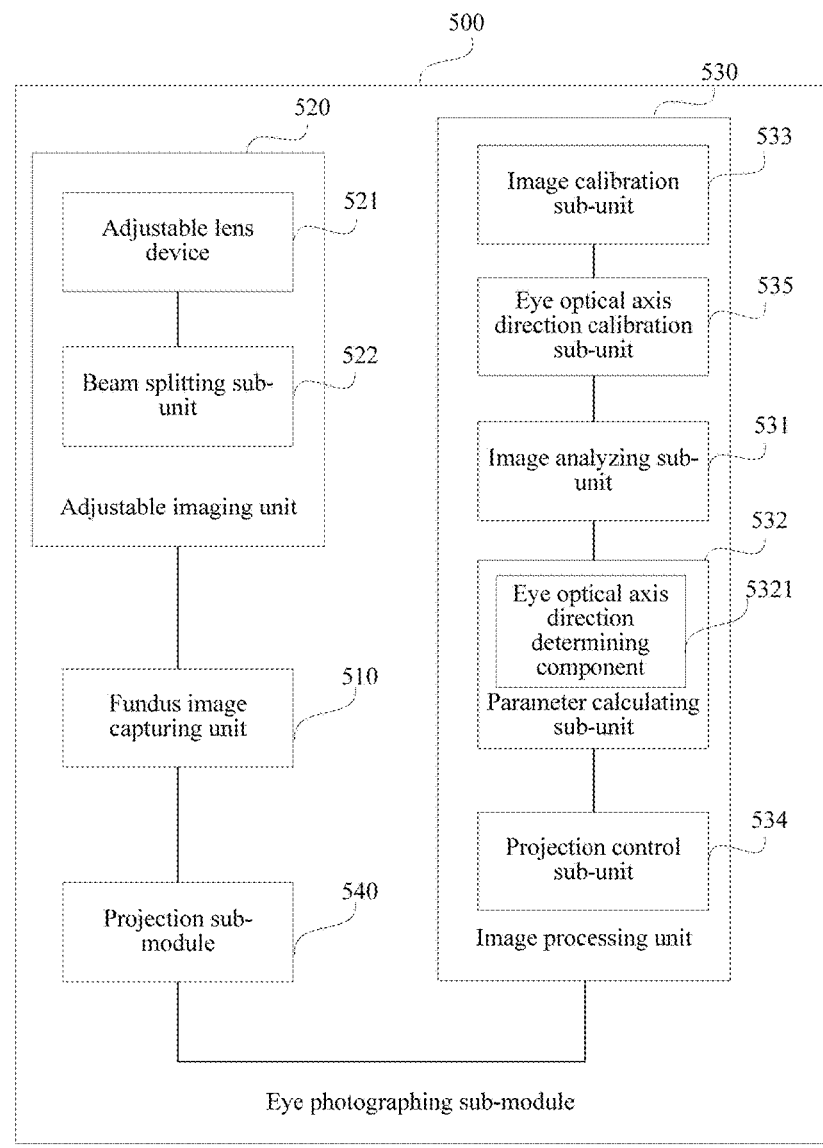
FIG. 5b is a schematic structural block diagram of another eye photographing sub-module according to an embodiment of the present application.

As shown in FIG. 5b, in a possible implementation of the embodiments of the present application, the fundus image capturing unit 510 is a micro camera, and in another possible implementation of the embodiments of the present application, a photosensitive imaging device, such as a CCD or a CMOS, may also be directly used as the fundus image capturing sub-module 510.

In a possible implementation of the embodiments of the present application, the adjustable imaging unit 520 comprises: an adjustable lens device 521, located on the optical path between the eye and the fundus image capturing unit 510, and having an adjustable focal length and/or an adjustable position on the optical path. By using the adjustable lens device 521, a system equivalent focal length between the eye and the fundus image capturing unit 510 may be adjusted, and by adjusting the adjustable lens device 521, the fundus image capturing unit 510 captures a fundus image satisfying at least one set resolution criterion when the adjustable lens device 521 is at a certain position or in a certain state. In this implementation, the adjustable lens device 521 performs adjustment continuously in real time during detection.

In a possible implementation of the embodiments of the present application, the adjustable lens device 521 is a focal-length adjustable lens, configured to adjust the focal length thereof by adjusting the refractive index and/or shape thereof. Specifically: 1) the focal length is adjusted by adjusting the curvature of at least one side of the focal-length adjustable lens, for example, the curvature of the focal-length adjustable lens is adjusted by adding or reducing liquid medium in a cavity formed by two transparent layers; and 2) the focal length is adjusted by changing the refractive index of the focal-length adjustable lens, for example, a specific liquid crystal medium is filled in the focal-length adjustable lens, and arrangement of the liquid crystal medium is adjusted by adjusting a voltage of a corresponding electrode of the liquid crystal medium, thereby changing the refractive index of the focal-length adjustable lens.

In another possible implementation of the embodiments of the present application, the adjustable lens device 521 comprises: a lens assembly formed by multiple lenses, configured to adjust relative positions between lenses in the lens assembly so as to adjust the focal length of the lens assembly. The lens assembly may also comprise a lens having adjustable imaging parameters such as the focal length thereof.

In addition to changing optical path parameters of the eye photographing sub-module 500 by adjusting characteristics of the adjustable lens device 521 as described in the foregoing, the optical path parameters of the eye photographing sub-module 500 may also be changed by adjusting a position of the adjustable lens device 521 on the optical path.

In a possible implementation of the embodiments of the present application, to avoid affecting experience of the user viewing an observed object, and to enable the eye photographing sub-module 500 to be portably applied to a wearable device, the adjustable imaging unit 520 may also comprise: an beam splitting sub-unit 522, configured to form light transmission paths between the eye and the observed object and between the eye and the fundus image capturing unit 510. Therefore, the optical path can be folded to reduce the volume of the eye photographing sub-module and avoid affecting other visual experience of the user as far as possible.

In this implementation, the beam splitting sub-unit 522 comprises: a first beam splitting sub-unit, located between the eye and the observed object, and configured to transmit light from the observed object to the eye and transmit light from the eye to the fundus image capturing unit.

The first beam splitting sub-unit may be a beam splitter, a beam splitting optical waveguide (including an optical fibers) or another suitable beam splitting device.

In a possible implementation of the embodiment of the present application, the image processing unit 530 of the eye photographing sub-module comprises an optical path calibration unit, configured to calibrate the optical path of the eye photographing module, for example, align an optical axis of the optical path, to ensure the precision of the measurement.

In a possible implementation of the embodiments of the present application, the image processing unit 530 comprises:

an image analyzing sub-unit 531, configured to analyze the at least one fudus image, to find the fundus image satisfying at least one set resolution criterion; and a parameter calculating sub-unit 532, configured to calculate optical parameters of the eye according to the fundus image satisfying at least one set resolution criterion, and the known imaging parameters of the system when the fundus image satisfying at least one set resolution criterion is obtained.

In this implementation, by using the adjustable imaging unit 520, the fundus image capturing unit 510 can obtain the fundus image satisfying at least one set resolution criterion; however, the fundus image satisfying at least one set resolution criterion in the at least one fundus image needs to be found by using the image analyzing sub-unit 531, and at this time, the optical parameters of the eye can be calculated according to the fundus image satisfying at least one set resolution criterion and the known optical parameters of the system. The optical parameters of the eye may comprise an optical axis direction of the eye.

In a possible implementation of the embodiments of the present application, the eye photographing sub-module further comprises: a projection unit 540, configured to project a light spot to the fundus. In a possible implementation, the function of the projection unit 540 may be implemented by using a mini projector.

The projected light spot may have no specific patterns but is only used for lightening the fundus.

In a preferred implementation of the embodiments of the present application, the projected light spot comprises a pattern with abundant features. The pattern with abundant features may be conducive to detection, and improve the detection precision. FIG. 2a is an exemplary diagram of a light spot pattern 200, where the pattern may be formed by a light spot pattern generator, for example, frosted glass; and FIG. 2b shows a fundus image shot when the light spot pattern 200 is projected.

To avoid affecting normal viewing of the eye, the light spot is an infrared light spot invisible to the eye.

Moreover, in order to reduce interference of other spectrums:

an emergent surface of the projection unit 540 may be provided with an eye-invisible light transmission filter; and an incident surface of the fundus image capturing unit 510 is provided with an eye-invisible light transmission filter.

In a possible implementation of the embodiments of the present application, the image processing unit 530 further comprises:

a projection control sub-unit 534, configured to control, according to a result obtained by the image analyzing sub-unit, the brightness of the light spot projected by the projection unit.

For example, the projection control sub-unit 534 may self-adaptively adjust the brightness according to characteristics of the image captured by the fundus image capturing unit 510. Here, the characteristics of the image include the contrast of image features, texture features, and the like.

Here, a special situation of controlling the brightness of the light spot projected by the projection unit 540 is turning on or turning off the projection unit 540, for example, when the user gazes at a point continuously, the projection unit 540 may be turned off periodically; and when the fundus of the user is bright enough, a light-emitting source may be turned off, and the distance from the current eye gaze point to the eye is detected only using fundus information.

In addition, the projection control sub-unit 534 may further control the brightness of the light spot projected by the projection unit 540 according to ambient light.

In a possible implementation of the embodiments of the present application, the image processing unit 530 further comprises: an image calibration sub-unit 533, configured to calibrate a fundus image, to obtain at least one reference image corresponding to the image presented at the fundus.

The image analyzing sub-unit 531 performs comparison calculation on the at least one image captured by the fundus image capturing unit 530 and the reference image, to obtain the fundus image satisfying at least one set resolution criterion. Here, the fundus image satisfying at least one set resolution criterion may be an obtained image having a minimum difference with the reference image. In this implementation, a difference between the currently acquired image and the reference image is calculated by using an existing image processing algorithm, for example, using a classical phase difference automatic focusing algorithm.

In a possible implementation of the embodiments of the present application, the parameter calculating sub-unit 532 comprises:

an eye optical axis direction determining component 5321, configured to obtain the optical axis direction of the eye according to features of the eye when the fundus image satisfying at least one set resolution criterion is acquired.

The features of the eye may be acquired from the fundus image satisfying at least one set resolution criterion, or may be acquired in other manners. The optical axis direction of the eye is corresponding to a gaze direction of a sight line of the eye.

In a possible implementation of the embodiments of the present application, the eye optical axis direction determining component 5321 comprises: a first determining component, configured to obtain the optical axis direction of the eye according to features of the fundus when the fundus image satisfying at least one set resolution criterion is obtained. As compared with obtaining the optical axis direction of the eye according to features of the pupil and eyeball surface, determining the optical axis direction of the eye according to the features of the fundus is more precise.

When a light spot pattern is projected to the fundus, the area of the light spot pattern may be greater than that of a visible region of the fundus or smaller than that of the visible region of the fundus, and for the method for acquiring the optical axis direction of the eye in the two situations, reference may be made to the corresponding description in the method embodiment shown in FIG. 1.

In another possible implementation of the embodiments of the present application, the eye optical axis direction determining component 5321 comprises: a second determining component, configured to obtain the optical axis direction of the eye according to features of the pupil when the fundus image satisfying at least one set resolution criterion is obtained. Here, the features of the pupil may be acquired from the fundus image satisfying at least one set resolution criterion, and may also be acquired in other manners. Obtaining the optical axis direction of the eye according to the features of the pupil belongs to the prior art, and is not described in detail herein.

In a possible implementation of the embodiments of the present application, the image processing unit 530 further comprises: an eye optical axis direction calibration sub-unit 535, configured to calibrate the optical axis direction of the eye, to determine the optical axis direction of the eye more precisely.

In the method of the embodiments of the present application, the imaging parameters of the optical path between the eye and the fundus image capturing position comprise at least one fixed imaging parameter and at least one real-time imaging parameter, where the at least one real-time imaging parameter is parameter information about the optical device when the fundus image satisfying at least one set resolution criterion is acquired, and the parameter information may be obtained by means of real-time recording when the fundus image satisfying at least one set resolution criterion is acquired.

Figure 5C:
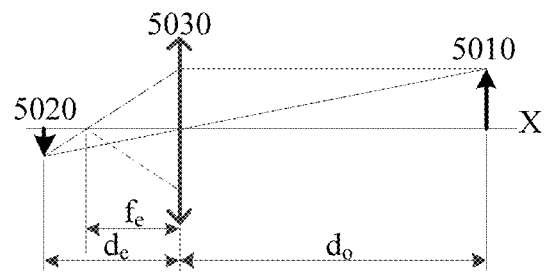
FIG. 5c is a schematic diagram of an optical path for eye imaging of an eye photographing sub-module according to an embodiment of the present application.

After the current optical parameters of the eye are obtained, the distance from the eye gaze point to the user may be calculated, and specifically:

FIG. 5c shows a schematic diagram of eye imaging, and in combination with a lens imaging formula in the classical optical theory, formula (1) may be obtained from FIG. 5c:

$$\frac{1}{d_o} + \frac{1}{d_e} + \frac{1}{f_e} \tag{1}$$

where $d_o$ and $d_e$ are respectively a distance from a current observed object 5010 of the eye to an eye equivalent lens 5030 and a distance from a real image 5020 on the retina to the eye equivalent lens 5030, $f_e$ is an equivalent focal length of the eye equivalent lens 5030, and X is a sight line direction of the eye (which may be obtained according to the optical axis direction of the eye).

Figure 5D:
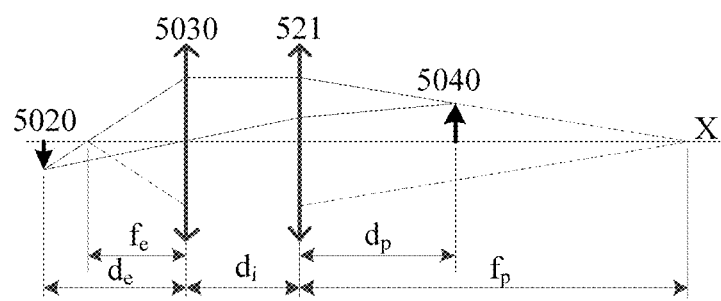
FIG. 5d is a schematic diagram of obtaining, according to known imaging parameters of a system and optical parameters of an eye, a position of an eye gaze point by an eye photographing sub-module according to an embodiment of the present application.

FIG. 5d shows a schematic diagram of obtaining a distance from an eye gaze point to the eye according to known optical parameters of the system and optical parameters of the eye. In FIG. 5d, a light spot 5040 forms a virtual image (not shown in FIG. 5d) through the adjustable lens device 521; assuming that a distance between the virtual image and the lens is X (not shown in FIG. 5d), the following equation set may be obtained in combination with formula (1):

$$\begin{cases} \frac{1}{d_p} - \frac{1}{x} = \frac{1}{f_p} \\ \frac{1}{d_i + x} + \frac{1}{d_e} = \frac{1}{f_e} \end{cases} \tag{2}$$

where $d_p$ is an optical equivalent distance from the light spot 5040 to the adjustable lens device 521, is an optical equivalent distance from the adjustable lens device 521 to the eye equivalent lens 5030, is a focal length value of the adjustable lens device 521, and is a distance from the eye equivalent lens 5030 to the adjustable lens device 521.

According to (1) and (2), a distance $d_o$ from the current observed object 5010 (eye gaze point) to the eye equivalent lens 5030 is as shown in formula (3):

$$d_o = d_i + \frac{d_p \cdot f_p}{f_p - d_p} \tag{3}$$

According to the distance from the observed object 5010 to the eye calculated above, and the optical axis direction of the eye obtained according to the foregoing description, the position of the eye gaze point may be obtained easily, providing a basis for subsequent further interaction related to the eye.

Figure 6:
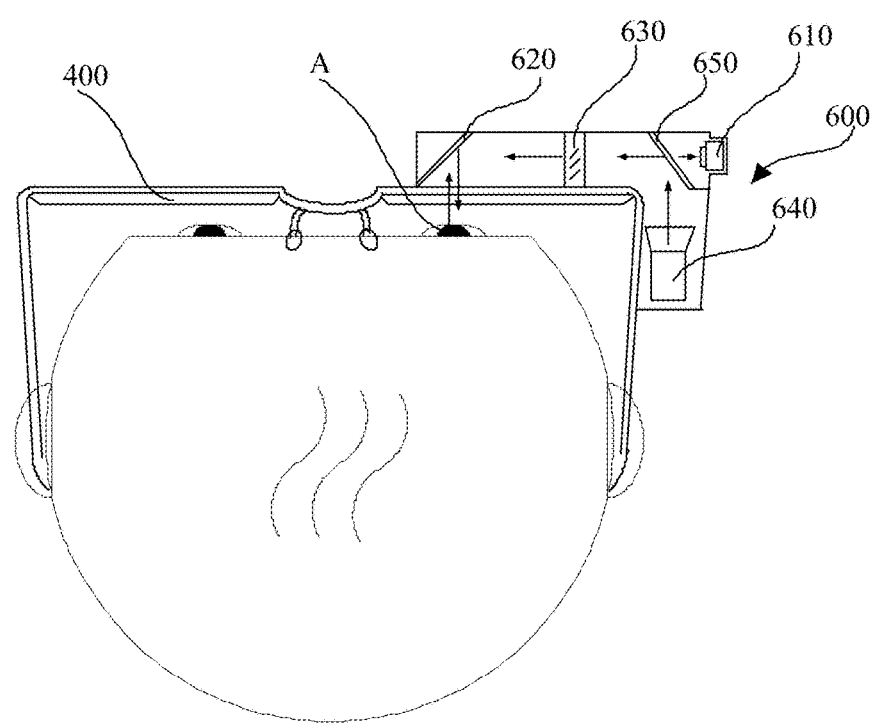
FIG. 6 is a schematic diagram of applying an eye photographing sub-module to a pair of glasses according to an embodiment of the present application.

FIG. 6 shows an embodiment of applying an eye photographing sub-module 600 according to a possible implementation of an embodiment of the present application to a pair of glasses 400, which comprises content described in the implementation shown in FIG. 5b, and specifically, it can be seen from FIG. 6 that, in this implementation, the apparatus 600 of this implementation is integrated to the right side (not limited thereto) of the glasses 400, and comprises:

a micro camera 610, which functions the same as the fundus image capturing unit described in the implementation of FIG. 5b, and is disposed at the outer right side of the glasses 400 to avoid affecting the sight line of normal viewing of the user;

a first beam splitter 620, which functions the same as the first beam splitting sub-unit described in the implementation of FIG. 5b, is disposed with a certain inclination angle at an intersection of a gaze direction of an eye A and an incident direction of the camera 610, and transmits light from an observed object to the eye A and reflects light from the eye to the camera 610; and a focal-length adjustable lens 630, which functions the same as the focal-length adjustable lens described in the implementation of FIG. 5b, is located between the first beam splitter 620 and the camera 610, and adjusts a focal length value in real time, so that the camera 610 can shoot a fundus image satisfying at least one set resolution criterion at a certain focal length value.

In this implementation, the image processing unit is not shown in FIG. 6, and functions the same as the image processing sub-module shown in FIG. 5b.

Generally, the brightness at the fundus is insufficient, and therefore, the fundus is lightened preferably. In this implementation, a light-emitting source 640 is used to lighten the fundus. The light-emitting source 640 is preferably an invisible light-emitting source, so as to avoid affecting the experience of the user, and preferably, a near-infrared light-emitting source which has small impact on the eye A and to which the camera 610 is relatively sensitive is used.

In this implementation, the light-emitting source 640 is located at the outer side of a spectacle frame at the right side, and therefore, a second beam splitter 650 together with the first beam splitter 620 is required to transmit light emitted by the light-emitting source 640 to the fundus. In this implementation, the second beam splitter 650 is located in front of the incident surface of the camera 610, and therefore, the incident surface further needs to transmit the light from the fundus to the second beam splitter 650.

It can be seen that, in this implementation, in order to improve the user experience and improve the capture definition of the camera 610, the first beam splitter 620 may preferably have characteristics of high reflectivity to infrared and high transmissivity to visible light. For example, an infrared reflective film may be set at one side of the first beam splitter 620 facing the eye A, so as to implement the foregoing characteristics.

It can be seen from FIG. 6 that, in this implementation, the eye photographing sub-module 600 is located at one side, away from the eye A, of the lens of the glasses 400, and therefore, when the optical parameters of the eye are calculated, the lens can be considered as a part of the eye A, and it is unnecessary to know optical characteristics of the lens.

In other implementations of the embodiment of the present application, the eye photographing sub-module 600 may be located at one side, near the eye A, of the lens of the glasses 400, and at this time, it is required to obtain optical characteristic parameters of the lens, and influencing factors of the lens are taken into consideration when a gaze point distance is calculated.

In this embodiment, the light emitted by the light-emitting source 640 is reflected by the second beam splitter 650, projected by the focal-length adjustable lens 630, reflected by the first beam splitter 620, then transmits through the lens of the glasses 400 to enter into the eye of the user, and finally reaches the retina at the fundus. The camera 610 shoots a fundus image through the pupil of the eye A along an optical path formed by the first beam splitter 620, the focal-length adjustable lens 630 and the second beam splitter 650.

Figure 7:
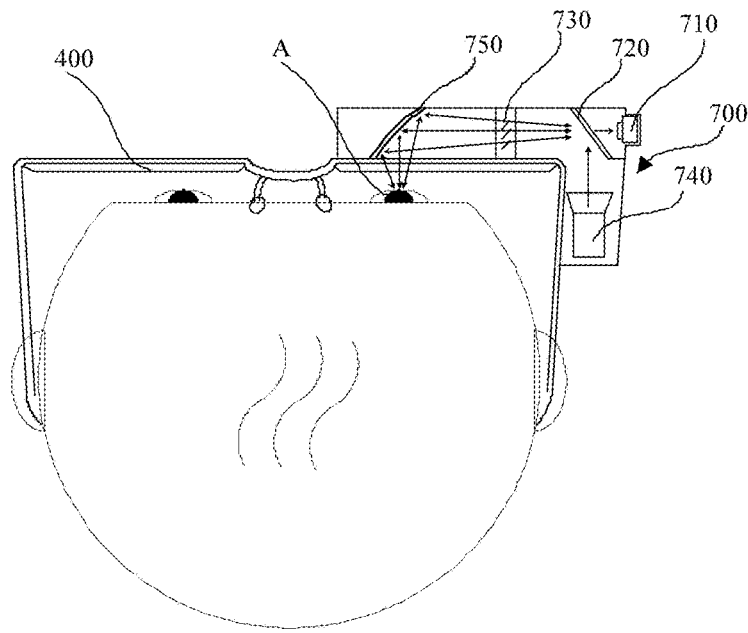
FIG. 7 is a schematic diagram of applying another eye photographing sub-module to a pair of glasses according to an embodiment of the present application.

FIG. 7 is a schematic structural diagram of another implementation of an eye photographing sub-module 700 according to another embodiment of the present application. It can be seen from FIG. 7 that, this implementation is similar to the implementation shown in FIG. 6, and comprises a micro camera 710, a second beam splitter 720, and a focal-length adjustable lens 730; this implementation differs from the implementation shown in FIG. 6 in that, a projection unit 740 in this implementation is the projection unit 740 for projecting a light spot pattern, and a curved-surface beam splitter 750, used as a curved-surface beam splitting device, replaces the first beam splitter in the implementation of FIG. 6.

The curved-surface beam splitter 750 separately corresponds to pupil positions associated with different optical axis directions of the eye, and transmits an image presented at the fundus to the fundus image capturing sub-module. In this way, the camera can capture mixed and superimposed eyeball images formed at various angles. However, only the fundus part passing through the pupil can be imaged clearly on the camera, and other parts are out of focus and cannot be imaged clearly, and do not severely affecting the imaging of the fundus part; therefore, features of the fundus part can still be detected. As a result, compared with the implementation shown in FIG. 6, this implementation can obtain good fundus images when the eye is gazing at different directions, so that the eye photographing module of this implementation has a broader application range and higher detection precision.

In a possible implementation of the embodiments of the present application, the apparatus is a pair of smart glasses. The camera of the smart glasses is very close to the eye of the user, and it can be considered that an image captured by the camera is the image that should appear in the visual field of the user, and correction between the image capturing position and the user position is not required, so that the user positioning is more natural and precise.

In a possible implementation of the embodiments of the present application, if the sight line direction of the user (for example, the distance acquired by means of ultrasonic waves) is not acquired when the distance acquisition module 340 is used, the apparatus of the embodiment of the present application may further comprise:

a sight line direction acquisition module 3100, configured to acquire the sight line direction of the user.

In the prior art, there are many methods for acquiring the sight line direction of the user, which are not described in detail herein. In the embodiment of the present application, as described in the embodiment shown in FIG. 5a to FIG. 5d, the function of the sight line direction acquisition module 3100 and the function of the eye photographing sub-module may be implemented by using the same device, that is: the sight line direction acquisition module 3100 and the eye photographing sub-module are the same module; and the optical parameters of the eye obtained by the image processing unit comprise the sight line direction of the user.

In one embodiment of the present application, the functions of the positioning module 360 are implemented according to the corresponding descriptions in the embodiments shown in FIG. 1 and FIG. 3, which are not described in detail herein.

In addition, an embodiment of the present application further provides a computer readable medium, comprising computer readable instructions for performing the following operations when being executed: operations of the S110, S120, S130, S140, S150 and S160 of the method in the foregoing embodiment.

Figure 8:
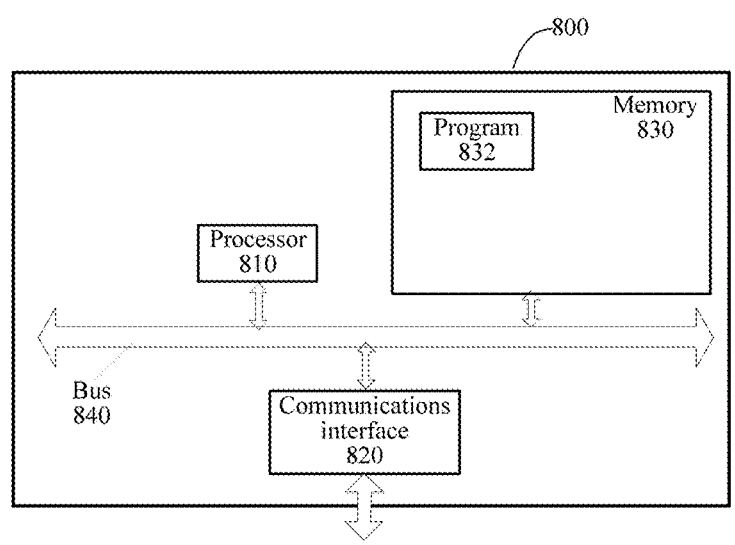
FIG. 8 is a schematic structural diagram of another positioning system according to an embodiment of the present application.

FIG. 8 is a schematic structural diagram of still another positioning system 800 according to an embodiment of the present application, and specific implementation of the positioning system 800 is not limited in the specific embodiment of the present application. As shown in FIG. 8, the positioning system 800 may comprise:

a processor 810, a communications interface 820, a memory 830, and a communication bus 840.

The processor 810, the communications interface 820 and the memory 830 communicate with each other through the communication bus 840.

The communications interface 820 is configured to communicate with a network element such as a client.

The processor 810 is configured to execute a program 832, and specifically, the processor may execute related steps in the method embodiments shown in FIG. 1 to FIG. 3.

Specifically, the program 832 may comprise program code, and the program code comprises computer operation instructions.

The processor 810 may be a central processing unit (CPU), or an application specific integrated circuit (ASIC), or is configured as one or more integrated circuits for implementing the embodiment of the present application.

The memory 830 is configured to store the program 832. The memory 830 may comprise a high-speed RAM memory, and may also comprise a non-volatile memory, for example, at least one magnetic disk memory. Specifically, the program 832 may enable the positioning system to perform the following operations:

acquiring a reference direction corresponding to a user;
determining that an eye of the user is gazing at an auxiliary positioning object;
acquiring position information of the auxiliary positioning object;
acquiring a distance of the user relative to the auxiliary positioning object;
acquiring an angle of a sight line direction of the user relative to the reference direction; and
obtaining position information of the user according to the position information of the auxiliary positioning object, the distance of the user relative to the auxiliary positioning object, the reference direction, and the angle of the sight line direction of the user relative to the reference direction.

For specific implementations of the units in the program 832, reference may be made to the corresponding units in the embodiments shown in FIG. 4 to FIG. 7, which are not described in detail herein. Persons skilled in the art may clearly know that, to make the description easy and concise, specific working processes of the devices and modules are not described in detail herein, and for details, reference may be made to the corresponding process descriptions in the method embodiments.

Persons of ordinary skill in the art may aware that, the units and method steps of various examples described in the embodiments disclosed in this text may be implemented by using electronic hardware, or a combination of computer software and electronic hardware. Whether the functions are executed in a hardware or software form depends on specific applications and design constraints of the technical solutions. For every specific application, persons skilled in the art may implement the described function by using different methods; however, the implementation should not be considered as exceeding the scope of the present application.

If the function is implemented in a form of a software function unit and is sold or used as an independent product, the software function unit may be stored in a computer readable storage medium. Based on this understanding, the technical solution of the present application essentially, or parts contributive to the prior art, or parts of the technical solution may be embodied in a form of a software product, the computer software product is stored in a storage medium comprising several instructions for enabling a computer device (such as a personal computer, a server, or a network device) to execute all or a part of steps of the method described in the embodiments of the present application. The storage medium comprises: a USB flash disk, a mobile hard disk, a Read-Only Memory (ROM), a Random Access Memory (RAM), a magnetic disk, an optical disc, or another medium capable of storing the program code.

The implementations are only used for describing the present application, instead of limiting the present application, and persons of ordinary skill in the art can make various changes and variations without departing from the spirit and scope of the present application, and therefore, all equivalent technical solutions fall within the scope of the present application, and the protection scope of the present application is defined by the claims.

What is claimed is:

1. A positioning method, comprising:
  acquiring a reference direction corresponding to a user by using a direction sensor;
  determining that an eye of the user is gazing at an auxiliary positioning object;
  acquiring position information of the auxiliary positioning object;
  acquiring a distance of the user relative to the auxiliary positioning object;
  acquiring an angle of a sight line direction of the user relative to the reference direction; and
  obtaining position information of the user according to the position information of the auxiliary positioning object, the distance of the user relative to the auxiliary positioning object, the reference direction, and the angle of the sight line direction of the user relative to the reference direction,
  wherein the position information of the auxiliary positioning object is three-dimensional position information of the auxiliary positioning object in a three-dimensional space,
  wherein the acquiring a distance of the user relative to the auxiliary positioning object comprises: in response to the eye of the user being gazing at the auxiliary positioning object, photographing the eye of the user to acquire the distance of the user relative to the auxiliary positioning object, and
  wherein the photographing the eye of the user to acquire the distance of the user relative to the auxiliary positioning object comprises: capturing at least one fundus image of the eye; adjusting at least one imaging parameter of an optical path between a fundus image capturing position of the at least one fundus image and the eye, until a fundus image satisfying at least one set resolution criterion in the at least one fundus image is captured; analyzing the at least one fundus image, to obtain imaging parameters of the optical path and optical parameters of the eye corresponding to the fundus image; and acquiring a distance of a current gaze point of the user relative to the user according to the imaging parameters and the optical parameters of the eye.

2. The method according to claim 1, further comprising: capturing at least one image comprising the auxiliary positioning object,
  wherein the acquiring position information of the auxiliary positioning object comprises: acquiring the position information of the auxiliary positioning object according to the at least one image.

3. The method according to claim 2, wherein the acquiring position information of the auxiliary positioning object comprises:

sending the at least one image to an external device; and
receiving, from the external device, the position information of the auxiliary positioning object.

4. The method according to claim 2, wherein the acquiring position information of the auxiliary positioning object comprises:
recognizing the auxiliary positioning object in the at least one image; and acquiring pre-stored position information of the auxiliary positioning object.

5. The method according to claim 1, wherein the adjusting at least one imaging parameter of an optical path between a fundus image capturing position and the eye, until a fundus image satisfying at least one set resolution criterion is captured comprises:
adjusting at least one of a focal length and a position of at least one optical device on the optical path.

6. The method according to claim 1, wherein the adjusting at least one imaging parameter of an optical path between a
fundus image capturing position and the eye, until a fundus image satisfying at least one set resolution criterion is captured comprises: transmitting an image presented at the fundus to the fundus image capturing position, corresponding to pupil positions associated with different optical axis directions of the eye.

7. The method according to claim 1, wherein the photographing the eye of the user to acquire the distance of the user relative to the auxiliary positioning object further comprises:
projecting a light spot pattern to the fundus.

8. The method according to claim 1, further comprising: acquiring the sight line direction of the user.

9. The method according to claim 8, wherein the optical parameters of the eye comprise the sight line direction of the user.

10. The method according to claim 1, comprising: guiding the user to gaze at the auxiliary positioning object.

11. The method according to claim 10, wherein the guiding the user to gaze at the auxiliary positioning object further comprises:
marking the auxiliary positioning object.

12. The method according to claim 11, wherein the guiding the user to gaze at the auxiliary positioning object further comprises:
marking the auxiliary positioning object by means of augmented reality.

13. A positioning system, comprising:
a reference direction acquisition module, configured to acquire a reference direction corresponding to a user; a gaze determining module, configured to determine that an eye of the user is gazing at an auxiliary positioning object;
an object information acquisition module, configured to acquire position information of the auxiliary positioning object with a direction sensor;
a distance acquisition module, configured to acquire a distance of the user relative to the auxiliary positioning object;
an angle acquisition module, configured to acquire an angle of a sight line direction of the user relative to the reference direction; and
a positioning module, configured to obtain position information of the user according to the position information of the auxiliary positioning object, the distance of the user relative to the auxiliary positioning object, the reference direction, and the angle of the sight line direction of the user relative to the reference direction,
wherein the position information of the auxiliary positioning object is three-dimensional position information of the auxiliary positioning object in a three-dimensional space,
wherein the distance acquisition module comprises: an eye photographing sub-module, configured to: in response to the eye of the user being gazing at the auxiliary positioning object, photograph the eye of the user to acquire the distance of the user relative to the auxiliary positioning object, and
wherein the eye photographing sub-module comprises: a fundus image capturing unit, configured to capture at least one fundus image of the eye; an adjustable imaging unit, configured to adjust at least one imaging parameter of an optical path between the fundus image capturing unit and the eye, until a fundus image satisfying at least one set resolution criterion in the at least one fundus image is captured; and an image processing unit, configured to analyze the at least one fundus image, to obtain imaging parameters of the optical path and optical parameters of the eye corresponding to the fundus image, and acquiring a distance of a current gaze point of the user relative to the user according to the imaging parameters and the optical parameters of the eye.

14. The system according to claim 13, further comprising: an image capturing module, configured to
capture at least one image comprising the auxiliary positioning object, wherein the object information acquisition module is further configured to obtain the position information of the auxiliary positioning object according to the at least one image.

15. The system according to claim 14, wherein the object information acquisition module comprises a communication unit, configured to:
send the at least one image to an external device; and receive, from the external device, the position information of the auxiliary positioning object.

16. The system according to claim 14, wherein the object information acquisition module comprises:
an object recognition unit, configured to recognize the auxiliary positioning object in the at least one image; and
a pre-stored information acquisition unit, configured to acquire pre-stored position information of the auxiliary positioning object.

17. The system according to claim 13, wherein the adjustable imaging unit comprises:
at least one adjustable lens device, having at least one of an adjustable imaging parameter and an adjustable position on the optical path.

18. The system according to claim 13, wherein the adjustable imaging unit further comprises:
a curved-surface beam splitting device, configured to transmit an image presented at the fundus to the image capturing unit, corresponding to pupil positions associated with different optical axis directions of the eye.

19. The system according to claim 13, wherein the eye photographing sub-module further comprises:
a projection unit, configured to project a light spot pattern to the fundus.

20. The system according to claim 13, further comprising: a sight line direction acquisition module, configured to acquire a sight line direction of the user.

21. The system according to claim 20, wherein the eye photographing sub-module comprise the sight line direction acquisition module; and the optical parameters of the eye obtained by the image processing unit comprise the sight line direction of the user.

22. The system according to claim 13, further comprising: an object guiding module, configured to guide the user to gaze at the auxiliary positioning object.

23. The system according to claim 22, wherein the object guiding module further comprises:
an object marking unit, configured to mark the auxiliary positioning object.

24. The system according to claim 23, wherein the object marking unit comprises:
an augmented reality marking sub-unit, configured to mark the auxiliary positioning object by means of augmented reality.

25. The system according to claim 13, wherein the system is a wearable device.

26. The system according to claim 25, wherein the system is a pair of smart glasses.

27. A non-transitory computer-readable storage medium, comprising executable instructions, wherein when a central processing unit of a positioning apparatus executes the executable instructions, the executable instructions are used for enabling the positioning apparatus to execute the following method:
acquiring a reference direction corresponding to a user by using a direction sensor; determining that an eye of the user is gazing at an auxiliary positioning object; acquiring position information of the auxiliary positioning object;
acquiring a distance of the user relative to the auxiliary positioning object; acquiring an angle of a sight line direction of the user relative to the reference direction; and obtaining position information of the user according to the position information of the auxiliary positioning object, the distance of the user relative to the auxiliary positioning object, the reference direction, and the angle of the sight line direction of the user relative to the reference direction,
wherein the position information of the auxiliary positioning object is three-dimensional position information of the auxiliary positioning object in a three-dimensional space,
wherein the acquiring a distance of the user relative to the auxiliary positioning object comprises: in response to the eye of the user being gazing at the auxiliary positioning object, photographing the eye of the user to acquire the distance of the user relative to the auxiliary positioning object, and
wherein the photographing the eye of the user to acquire the distance of the user relative to the auxiliary positioning object comprises: capturing at least one fundus image of the eye; adjusting at least one imaging parameter of an optical path between a fundus image capturing position of the at least one fundus image and the eye, until a fundus image satisfying at least one set resolution criterion in the at least one fundus image is captured; analyzing the at least one fundus image, to obtain imaging parameters of the optical path and optical parameters of the eye corresponding to the fundus image; and acquiring a distance of a current gaze point of the user relative to the user according to the imaging parameters and the optical parameters of the eye.

28. A positioning apparatus, comprising a central processing unit and a memory, wherein the memory stores computer executable instructions and the central processing unit is connected to the memory through a communication bus, and when the central processing unit executes the computer executable instructions stored in the memory, the positioning apparatus performs the following method:
acquiring a reference direction corresponding to a user by using a direction sensor; determining that an eye of the user is gazing at an auxiliary positioning object; acquiring position information of the auxiliary positioning object;
acquiring a distance of the user relative to the auxiliary positioning object; acquiring an angle of a sight line direction of the user relative to the reference direction; and obtaining position information of the user according to the position information of the auxiliary positioning object, the distance of the user relative to the auxiliary positioning object, the reference direction, and the angle of the sight line direction of the user relative to the reference direction,
wherein the position information of the auxiliary positioning object is three-dimensional position information of the auxiliary positioning object in a three-dimensional space,
wherein the acquiring a distance of the user relative to the auxiliary positioning object comprises: in response to the eye of the user being gazing at the auxiliary positioning object, photographing the eye of the user to acquire the distance of the user relative to the auxiliary positioning object, and
wherein the photographing the eye of the user to acquire the distance of the user relative to the auxiliary positioning object comprises: capturing at least one fundus image of the eye; adjusting at least one imaging parameter of an optical path between a fundus image capturing position of the at least one fundus image and the eye, until a fundus image satisfying at least one set resolution criterion in the at least one fundus image is captured; analyzing the at least one fundus image, to obtain imaging parameters of the optical path and optical parameters of the eye corresponding to the fundus image; and acquiring a distance of a current gaze point of the user relative to the user according to the imaging parameters and the optical parameters of the eye.

* * * * *